United States Patent
Glozman et al.

(10) Patent No.: US 8,484,001 B2
(45) Date of Patent: Jul. 9, 2013

(54) PRE-OPERATIVE MEDICAL PLANNING SYSTEM AND METHOD FOR USE THEREOF

(75) Inventors: Zeev Glozman, Tel Aviv (IL); Meron Liram, Rehovot (IL); Doron Norman, Haifa (IL)

(73) Assignee: Voyant Health Ltd., Petach-Tikva (IL)

( * ) Notice: Subject to any disclaimer, the term of this patent is extended or adjusted under 35 U.S.C. 154(b) by 135 days.

(21) Appl. No.: 10/647,796

(22) Filed: Aug. 26, 2003

(65) Prior Publication Data
US 2005/0059873 A1    Mar. 17, 2005

(51) Int. Cl.
*G06G 7/48* (2006.01)

(52) U.S. Cl.
USPC .............................................. 703/6

(58) Field of Classification Search
USPC ............. 703/6, 7, 11; 600/407, 427; 382/128, 382/132
See application file for complete search history.

(56) References Cited

U.S. PATENT DOCUMENTS

| | | | |
|---|---|---|---|
| 5,016,173 A * | 5/1991 | Kenet et al. | 382/128 |
| 5,263,074 A * | 11/1993 | Sakamoto | 378/98.2 |
| 5,748,767 A | 5/1998 | Raab | |
| 5,769,092 A | 6/1998 | Williamson, Jr. | |
| 6,205,411 B1 * | 3/2001 | DiGioia et al. | 703/11 |
| 6,281,944 B1 * | 8/2001 | Kim | 348/674 |
| 6,285,902 B1 * | 9/2001 | Kienzle et al. | 600/427 |
| 6,701,174 B1 * | 3/2004 | Krause et al. | 600/407 |
| 6,711,432 B1 * | 3/2004 | Weiss et al. | 600/427 |
| 7,440,599 B2 * | 10/2008 | Kato | 382/128 |
| 2005/0267722 A1 * | 12/2005 | Marquart et al. | 703/11 |

OTHER PUBLICATIONS

Hanson et al., "OrthoDock—An Image Driven Orthopaedic Surgical Planning System", Proceedings of Twelfth Annual International Conference of the IEEE Engineering in Medicine and Biology Society, Nov. 1990, pp. 1931-1932.*

Kazanzides et al., "An Integrated System for Cementless Hip Replacement", IEEE Engineering in Medicine and Biology Magazine, May/Jun. 1995, pp. 307-313.*

Shahidi et al., "Clinical Applications of Three-Dimensional Rendering of Medical Data Sets", Proceedings of the IEEE, Mar. 1998, pp. 555-568.*

* cited by examiner

*Primary Examiner* — Omar Fernandez Rivas
*Assistant Examiner* — Herng-der Day

(57) ABSTRACT

Method and apparatus for pre-operative planning of orthopedic surgical procedures. The pre operative planning includes the steps of image acquisition, calibration scaling and registration, fracture reduction or matching of prosthesis, application of fixation elements and creating of planning reports.

47 Claims, 12 Drawing Sheets

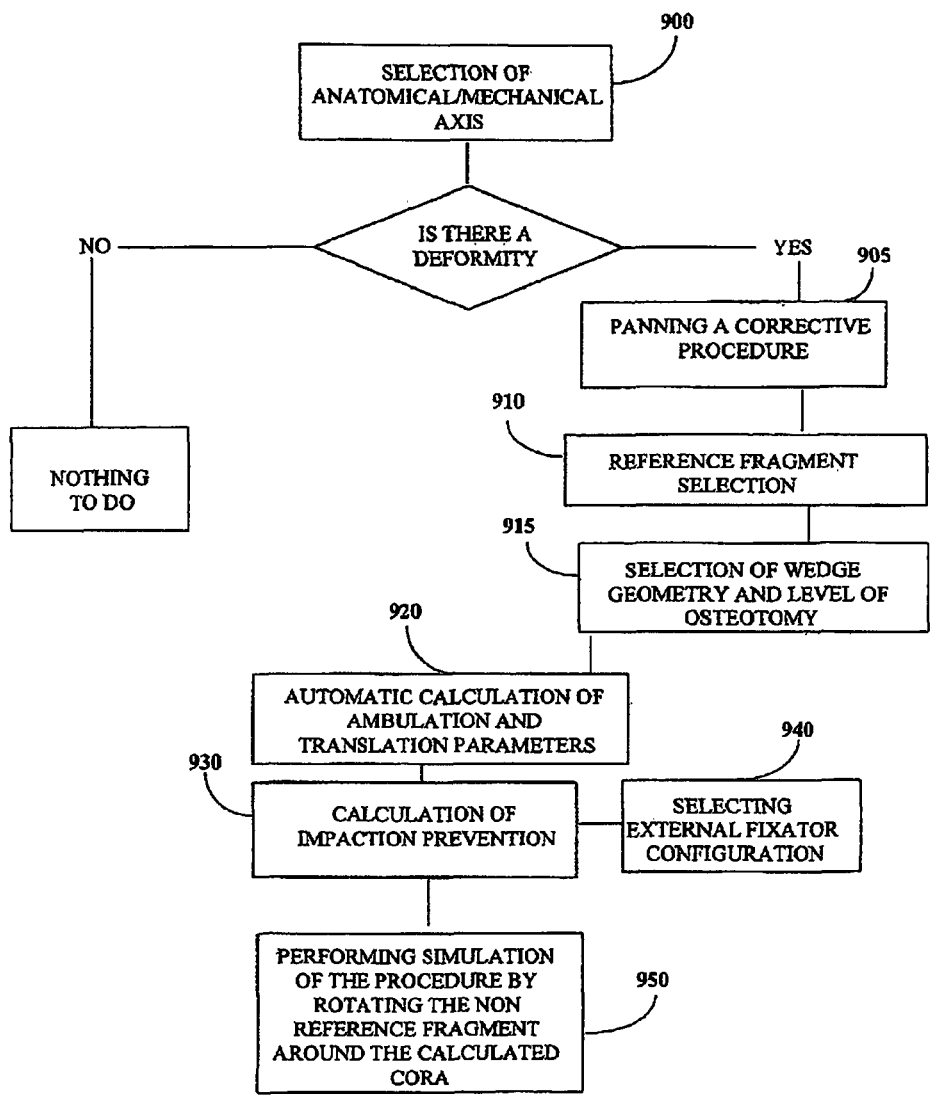

PRE-OPERATIVE MEDICAL PLANNING SYSTEM AND METHOD FOR USE THEREOF

FIELD OF THE INVENTION

The present invention relates to methods and apparatus for pre-operative planning of orthopaedic surgical procedures.

BACKGROUND OF THE INVENTION

Introduction of digital radiology poses a sufficient challenge to hospital radiology, but also the orthopaedic department. This field describes a system and method-allowing surgeons to perform tasks of medical image analysis using manual tools using a computer based software. Specifically, the need for such a tool exists in the field of orthopaedic surgical procedures. Surgeons are still accustomed to planning treatment of bone fractures by using two-dimensional conventional x-ray images.

The common practice in planning treatment for orthopaedic trauma includes copying bone fragments (hereinafter 'segments') from x-ray images onto separate pieces of transparent paper. It is done twice in order to have copies of bone segments in two projections (AP and Lateral). The different fragments (e.g., segments) are aligned together and glued in the required positions to achieve an anatomic fracture reduction. Over the reduced patterns, the surgeon attempts to match the best available fixation devices and elements using templates of these devices and elements.

For joint arthroplasty, a template of the prosthesis, which is supplied by the manufacturer, is aligned to the X-Ray images of the patient. Once a correct position and angle are achieved, the template is glued to the film. This can only be used as a rough guide for the surgical procedure since the scaling of the X-Ray image is such that it is not always an exact reproduction of the bone segment and optimal positioning of the prosthesis may not be parallel to the viewed angle of the images.

The traditional technique, which is performed as described hereinabove by aligning templates to printed X-Ray films, suffers from several disadvantages:

The dimensioning may not be representative of the actual object-scaling varies from 110%-120% of real size, due to a distorting effect known as divergence, whereas templates are supplied in fixed size.

There is difficulty in saving or printing out the results in an organized and cost-effective manner.

The planning is time-consuming and complicated.

Furthermore, introduction of advanced imaging techniques such as PACS systems will eliminate the handling of traditional X-Ray film from hospital centers. In such instances, the traditional pre-planning technique will require printout of X-Ray images on costly materials.

There is also another need that cannot be fulfilled using the traditional pre-planning technique, which is better control and education. It is common—for a chief surgeon to review and analyze procedures performed by his staff and explore multiple alternative treatments with his staff prior to the surgery.

U.S. Pat. No. 5,769,092 to Williamson presents a computer-assisted system to help perform a hip replacement. The system allows the surgeon to interact with 3D models of the relevant bones to select an appropriate replacement strategy. No registration of the anatomical structures of interest is available; the immobilization of the anatomical structures renders the intra-operating room planning to be difficult, since no trial movements can be performed on the immobilized structures. Moreover, Williamson's system does not allow the visualization of transparent 3D models of the anatomical structures. U.S. Pat. No. 5,748,767 to Raab discloses a computer-aided surgery apparatus adapted to aid a medical practitioner in positioning a surgical instrument or implant when performing surgery on or examining portions of a patient. Pre-treatment and treatment coordinates are continually calculated with respect to a specially designed reference block attached to an electrogoniometer, wherein a mechanical linkage for maintaining the surgical tool in a fixed relationship with the reference block is required. Such machinations of the probing process create a system that is relatively cumbersome for the practitioner using a hand-held transducer. Moreover, difficulty is obtained with which a prior imaging plane can be recaptured for comparison purposes, a problem which becomes even more significant with the use of hand-held transducer.

It is thus the purpose of the present invention to offer digital templating for pre-planning of orthopedic surgical procedures. It is the purpose of the present invention to allow the surgeon to calibrate the images, plan how to reduce the fracture or align implants, and apply fixation, using an interactive and user-friendly system. Additionally, it is the purpose of the present invention to enable review of various therapeutic options and have a better opportunity to choose the best. Additionally, the present invention enables the possibility of communication with operating room inventory systems. The present invention also enables producing reports, which include final pre planning images of reduced and fixed fractures as well as inventory, and part list reports. The further aspect of the present invention enables communicating of all data to and from other database systems.

SUMMARY OF THE INVENTION

The present invention relates to a method for pre-operative planning and simulation of orthopaedic surgical procedures using medical images. The method is comprised of the following steps: (a) obtaining medical images and making a composite view of an anatomical structure. This may be comprised of one or more images to provide a full-length view of the anatomical structure; (b) segmenting the anatomical structure—such as bone but not limited to bone segments—in the medical images, and manipulating the image segments to simulate a desired result of the orthopedic surgical procedure. (c) performing different measurements and analysis, such as length discrepancy, angle measurements, as well as more complex sets of measurements such as deformity analysis, structural relationship in terms of distances and angles to one another, (d) production of output images are wherein the obtained output images comprise features selected from the group of a plurality of n calibrated organs—a plurality of m organ segments; a plurality of j calibrated artificial elements wherein n, m, and j are integer numbers between 1 to 100; and/or at least one superposition of the calibrated artificial elements on the calibrated organs and/or organ segments. In one preferred embodiment of the present invention, the medical images are X-ray images. In another embodiment, the medical images are combination of plurality of imaging techniques. In yet another embodiment, the medical images comprise a plurality of views of the same organs. Preferably, the procurement stage is done by transforming of the medical images to digital images. The obtaining step may also be comprised calibrating of images. It is noted that calibrating of images may include registration of different views, calibration of dimension and orientation, and/or image enhancements such as brightness and contrast adjustments, and edge detection. Calibration may also involve correction of distortions. In another preferred embodiment of the present invention, the segmenting step is performed manually by a medical expert (In another preferred embodiment of the present invention, the segmenting step is performed automatically, in the manner that the anatomical structure segments are segmented according to predefined rules. In yet another preferred embodiment of the present invention, the segmenting step is performed semi-automatically, in the manner that the segmenting step is performed automatically with the assistance of a medical expert. Preferably, the planning step also comprises simulating various positioning of the anatomical structure segments. Different positioning of the anatomical structure segments relates to reducing of fractures during trauma treatment, or relates to pre-designed treatments for distorted anatomical structures. Preferably, the artificial elements comprise implants; in the manner that superposition of implants and the segmented anatomical structure over non-segmented fragments of the anatomical structure is provided. The artificial elements may also comprise fixation elements, in the manner that superposition of members selected from fixators, fixators anchoring devices, and the segmented anatomical structure over non-segmented fragments of the anatomical structure is provided. A preferred embodiment may comprise a step of choosing a plurality of the fixation elements from a predefined database, and rules for correct positioning of the fixation elements so incorrect positioning of the fixation elements is prevented. The above method may additionally comprise a step of producing and storing output images and planning reports of a (he uses this word too often) large number of alternatives of the steps of segmenting and planning, for the purpose that the best alternative for medical treatment is selected from the choices; the planning report may also comprise part definition of the artificial elements selected for the treatment. The above method may additionally comprise a step of providing hard copies of the output images and the planning reports of a selected set of the alternatives. The method also enables communicating the output images and the planning reports to a multitude of remote users.

The present invention also relates to an apparatus for pre planning and simulating of orthopedic surgical procedures using medical images which comprises: (a) segmenting means for defining and marking anatomical structure segments in the medical images, (b) planning means for planning the desired result of the orthopedic surgical procedure, which comprise means for producing output images, wherein the output images comprise features selected from the group of a plurality of n calibrated organs; a plurality of m organ segments; a plurality of j calibrated artificial elements wherein n,m,j are integer numbers between 1 to 100; and/or at least one superposition of the calibrated artificial elements on the calibrated organs and/or organ segments. (c) a memory for storing the medical images and the desired result, and (d) a display for displaying the medical images and the output images.

In one preferred embodiment of the present invention, the medical images are X-ray images. In another embodiment, the medical images are combination of plurality of imaging techniques. In yet another embodiment, the medical images comprise a plurality of views of the same organs The apparatus may further comprise means for transforming the medical images to digital images. The apparatus according to the present invention may additionally comprise calibration means for images. The calibration means may be utilized for registration of different views, for dimension and orientation calibration, and for image enhancements comprising brightness and contrast adjustments, and edge detection. The calibration means may also be utilized for correction of image distortions. The segmenting means of the above apparatus, may be manually operated by a medical expert, or they may be automatically operated according to predefined rules. Additionally, the segmenting means may also be operated semi-automatically in the manner that the segmenting step is performed automatically with the assistance of a medical expert. The planning means of the present invention are mainly utilized for simulating different positioning of the anatomical structure segments: simulating reduction of fractures during trauma treatment, and simulating pre-designed treatments for distorted organs. The artificial elements comprise implants; in the manner that superposition of implants and the segmented anatomical structure over non-segmented fragments of the anatomical structure is provided. The artificial elements also comprise fixation elements, in the manner that superposition of members selected from fixators, fixators anchoring devices, and the segmented anatomical structure over non-segmented fragments of the anatomical structure is provided. The apparatus of the present invention further comprises a predefined database comprising predefined sets of fixation elements. The apparatus may further comprise means for correct positioning of the fixation elements so incorrect positioning of the fixation elements is prevented. The apparatus according to the present invention may additionally comprise means for producing and storing output images and planning reports of plurality of alternatives, for the purpose that the best alternative for medical treatment is selected from the alternatives, and the planning reports comprise part definition of the artificial elements selected for the medical treatment. The apparatus according to the present invention may also comprise means for creating hard copies of the output images and the planning reports of a selected set of the alternatives. Additionally, the apparatus of the present invention may also comprise communicating means for communicating the output images and the planning reports to remote users.

BRIEF DESCRIPTION OF THE INVENTION

In order to understand the invention and to see how it may be implemented in practice, preferred embodiments will now be described, by way of non-limiting example only, with reference to the accompanying drawing, in which:

FIG. 9 is a flowchart of the process of osteotomy with artificial fixation devices in accordance with the present invention; and, FIG. 10 is a flowchart of image rendering in accordance with one embodiment of the present invention.

DETAILED DESCRIPTION OF THE INVENTION

Figure 1:
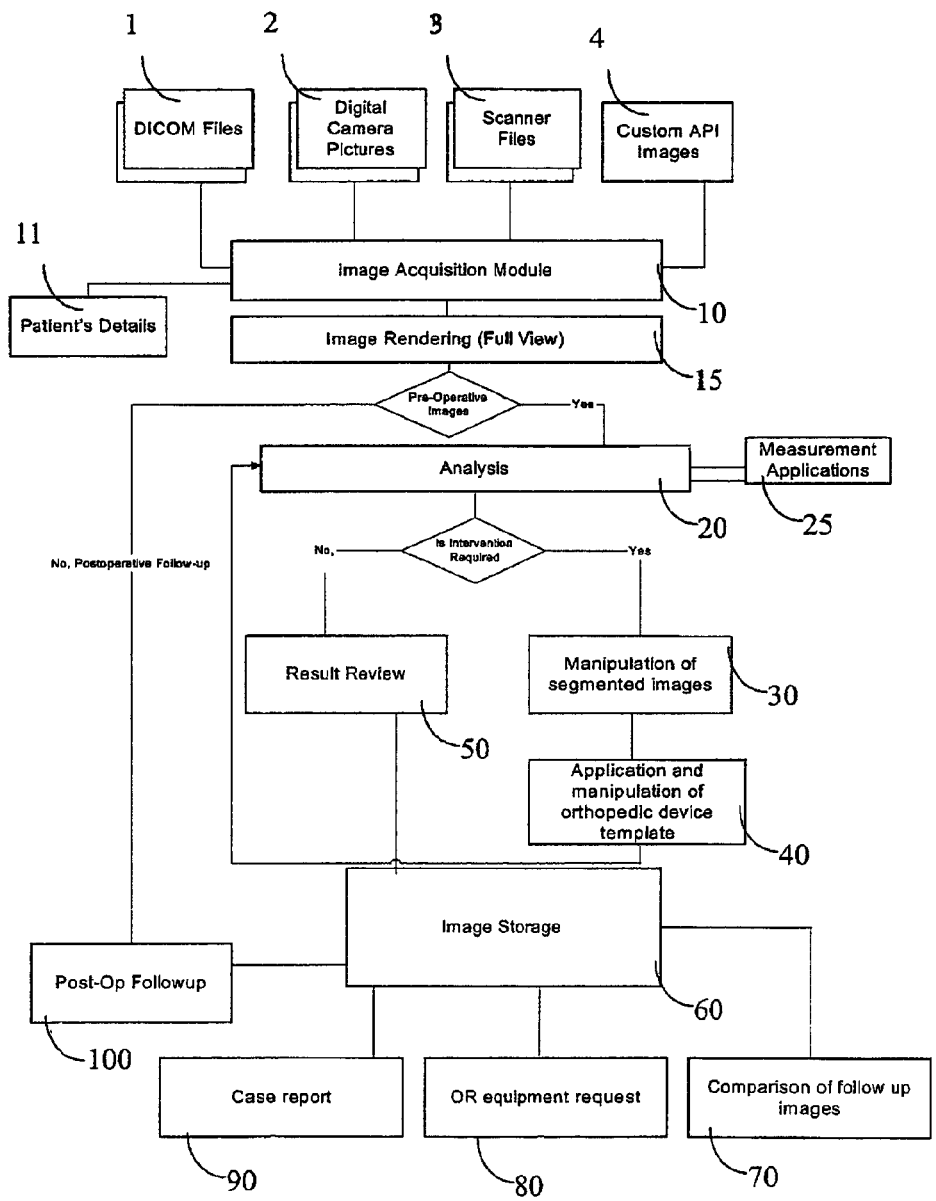
FIG. 1 is a flowchart of the process performed in the pre-planning system of the present invention.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide methods and apparatus for pre-operative planning of orthopedic surgical procedures.

The present invention is directed to a method for pre-planning and simulating of orthopaedic surgical procedures using medical images. The method comprises the following steps: (a) obtaining and displaying the medical images; (b) segmenting anatomical structure segments in the medical images; and (c) planning the desired result of the orthopaedic surgical procedure so output images are produced, wherein the obtained output images comprise features selected from the group of a plurality of n calibrated organs; a plurality of m organ segments; a plurality of j calibrated artificial elements wherein n, m, and j are integer numbers between 1 to 100; and/or at least one superposition of the calibrated artificial elements on the calibrated organs and/or organ segments.

The present invention also relates to an apparatus for pre planning and simulating of orthopaedic surgical procedures using medical images which comprises (a) segmenting means for defining and marking anatomical structure segments in the medical images, (b) planning means for planning the desired result of the orthopaedic surgical procedure, which comprise means for producing output images, wherein the output images comprise features selected from the group of a plurality of n calibrated organs; a plurality of m organ segments; a plurality of j calibrated artificial elements wherein n,m,j are integer numbers between 1 to 100; and/or at least one superposition of the calibrated artificial elements on the calibrated organs and/or organ segments. (c) a memory for storing the medical images and the desired result, and (d) a display for displaying the medical images and the output images.

The term 'anatomical structure segment' refers according to the present invention to any segment of a anatomical structure that is defined and marked by a physician or other medical expert for the purpose of referring to this anatomical structure separately from the other objects on the image. Segmenting anatomical structure segment is done by the action of defining and marking. According to the present invention, the action of segmenting may be performed manually using interactive computer means such as a mouse or any other pointing device. Segmenting according to other embodiments may be performed automatically or semi automatically as described hereinafter. The segmenting action results in digital anatomical structure segments that are marked on the display.

The term 'medical images' refers according to the present invention to standard medical images that are produced by medical imaging devices such as X-Ray, CT, MRI, and others.

The term 'result of orthopedic surgical procedure' refers according to the present invention to the desired outcome of the orthopedic surgical procedure such as reduced fracture. The term 'desire' generally refers to the recuperation, healing and/or recovery of the body's organ in correlation and/or agreement with the predetermined purposes and intentions of the aforementioned orthopedic procedure. The result as preplanned by the system of the present invention is demonstrated in the aforementioned output images.

The term 'output images' refers according to the present invention to pre-planning images that are produced by the present invention including fracture reduction positioning of broken bones and orthopedic implants and fixation elements.

The term 'orthopedic surgical procedure' refers according to the present invention to orthopedic operation for purposes such as bone fracture reduction.

The term 'fixators' refers according to the present invention to fixators, anchoring means, selected from screws, nails, anchors (plates), implants or any combination thereof.

Typically, the pre-planning system of the present invention will involve computer hardware and software, display, keyboard and pointing device (e.g., mouse), communication and hard copy devices. As the hardware components of the system may be standard computer components, it should be appreciated that the novelty of the present invention may be realized by software. However, special hardware devices may also be configured to the specific functions of the present invention.

Reference is made now to FIG. 1, presenting is a block diagram that illustrates in general the process performed by the pre operative planning system according to one embodiment of the present invention. Image Acquisition Module 10 receives images from various sources such as: DICOM Files 1, Digital Camera Pictures 2, Scanner Files 3, Custom API images 4, or any other source for medical images. Typically, X-Ray imaging is the common way to acquire images of hard tissues such as bones, however any medical imaging may be used for acquisition of the relevant medical images. X-Ray image on film may be scanned by a regular digital scanner to produce a digital Scanner file 3 of the image. Image Acquisition Module 10 is also responsible for calibration and scaling. Calibration and scaling may include various operations of image enhancements that are commonly used in displaying of images. Images may be enhanced by performing histogram equalization, brightness and contrast adjustments, edge detection, etc. Calibration and scaling may also include dimension calibration for registration with additional objects such as fixation elements as will be explained hereinafter. A common way for acquiring a real dimension unit in the image is to add an object of a known length to be imaged with the imaged subject. Calibration and scaling may also include correction for image distortion as many imaging devices create distortion during imaging. Distortion correction may be performed by applying non-linear correction functions on the original image. These functions are typical to an imaging device and once these functions are created, any image taken by the device may be corrected and the distortion may be reduced to an acceptable minimum. The next step to be performed by the Image Acquisition Module 10 of the pre-planning system of the present invention is creating mathematical relationship between the two projections or views of the organs. This mathematical relationship may be used for automatically updating one view when the other view is manually altered, or for creating three dimensional data structure of the objects in the images. Patient details 11 are attached to the medical images. Image Rendering 15 is a step in which separate images of different parts of an organ may be composed and integrated to a full image of the organ. This step will be further described hereinafter. Then, Analysis 20 is performed assisted by measurement applications 25. The analysis determines whether an intervention is required. In case an intervention is required, the next step is Manipulation of segmented images 30.

In case of a trauma, the common treatment in orthopaedic procedures is fracture reduction. Fracture reduction in accordance with the present invention will be described in details hereinafter. The next step is Application and manipulation fixation elements 40. During this step, fixation elements are selected from a predefined set of standard fixation elements, or customized and designed specifically for the special need of a particular procedure. A template on the display may include various elements of various parameters, and drag-and-drop, move, and rotate functions on the display may define and locate the fixation in the required place. The fixation element, after defined by the medical expert, will be displayed at the right size according to the scale of the image (e.g., zoom), with accordance to the actual dimension of the fixation element. Fixation elements may be also selected and defined using a special keyboard that may be designed for this system. Planning result 60 is the output of the process. Planning result 60 may include images describing the final desired result of the orthopedic procedure, inventory report of fixation elements that were selected for the procedure, other result alternatives that were not selected to be performed. Planning result 60 may be stored, reviewed, printed or communicated to other systems. Various outputs may be created from planning result 60 such as Case report 90, OR equipment request 80 and Comparison of follow up images 70. The system of the present invention may also be used for Post Op follow up 100 and for Result review 50 when an intervention is not required. In addition to trauma cases, the pre planning system of the present invention may also be used in other cases such as osteotomy as will be described in details hereinafter.

Figures 2A, 2B:
FIG. 2A is a schematic view of X-Ray image of a broken bone as displayed on the pre planning system of the present invention.
FIG. 2B is a schematic view of X-Ray image of a different view of a broken bone.

Reference in now made to FIG. 2A and FIG. 2B, that are schematics of X-Ray images of different views of a broken bone. A broken bone is a common case of trauma. The X-Ray images of FIGS. 2A and 2B represent medical X-Ray images displayed on the display of the pre planning system of the present invention. These X-Ray images at this step are already calibrated and registered as explained hereinbefore (FIG. 1). Bone 220 of FIG. 2A is also demonstrated in different view as bone 260 of FIG. 2B. Similarly, bone segments 200 and 210 of FIG. 2A are also demonstrated in different view as bone segments 240 and 250 of FIG. 2B correspondingly. Fracture 230 of FIG. 2A is also demonstrated in FIG. 2B as fracture 270. It is obvious that bone segments 200 and 210 of FIG. 2A, and corresponding bone segments 240 and 250 of FIG. 2B, are segments of the same bone that is broken to two segments. The preferred medical treatment should obviously include reducing the fracture and fix the bone segments together.

Reference is now made to FIGS. 3A, 3B, 4A and 4B that demonstrate the different steps composing pre planning of fracture reduction according to the present invention.

Figures 3A, 3B:
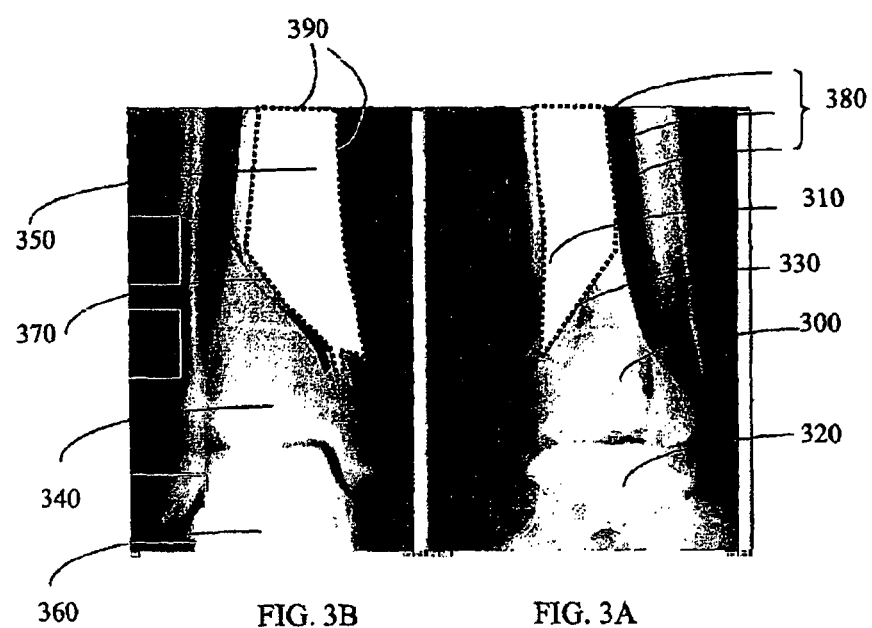
FIG. 3A is a schematic view of X-Ray image of a broken bone with marked bone segment.
FIG. 3B is a schematic view of X-Ray image of a different view of a broken bone with marked bone segment.

FIG. 3A and FIG. 3B demonstrate the step of defining and marking a bone segment of the image that will be relatively moved on the display in order to simulate a different location of an organ. In the trauma case described here, it is desired to move a bone segment 310 of FIG. 3A and similarly the same bone segment 350 of FIG. 3B in order to reduce a bone fracture. Bone segments 300 and 320 of FIG. 3A and corresponding bone segments 340 and 360 of FIG. 3B are not marked in this case. Marks 380 of FIG. 3A and marks 390 of FIG. 3B are inserted to the images manually by the medical expert. Alternatively, defining and marking of segments may be performed automatically by the preplanning system of the present invention using image processing techniques such as pattern recognition. Yet another option is that defining and marking is performed semi automatically by the pre planning system with interactive assistance of the medical expert.

Figures 4A, 4B:
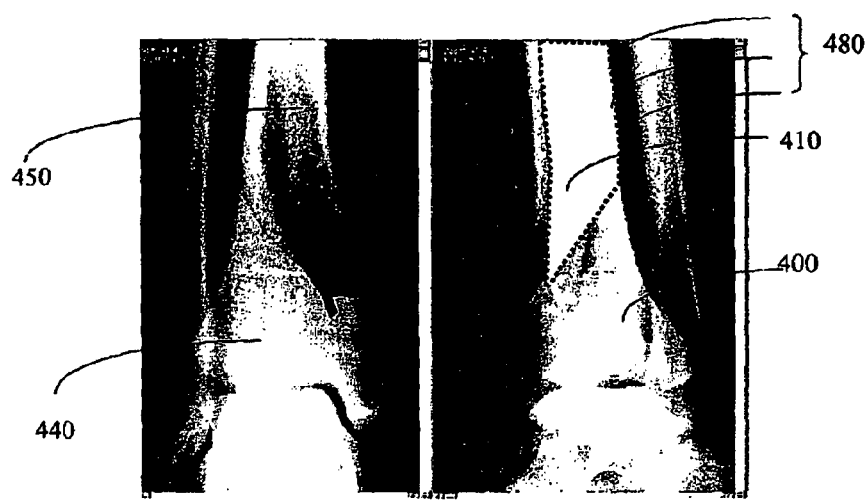
FIG. 4A is a schematic view of X-Ray image of a reduced fracture.
FIG. 4B is a schematic view of X-Ray image of a different view of a reduced fracture.

FIGS. 4A and 4B are schematic views of X-Ray image of a reduced fracture. Bone segment 310 Of FIG. 3A is moved to a new location on the image. The new location is demonstrated in FIG. 4A, and the moved segment 410 is still marked by marks 480. The medical expert is using standard interactive drag-and-drop capability to interactively move segment 410 on the display. It is obvious on FIG. 4A that the fracture has been reduced and bone segments 400 and 410 are located as close as possible to the original situation before the bone was broken to the two said segments.

FIG. 4B illustrates a different view of the reduced fracture of FIG. 4A. The marks are not presented in order to improve observation of detail during the pre planning. The marks can be displayed or alternatively removed on both views as requested by the medical expert.

Figures 5A, 5B:
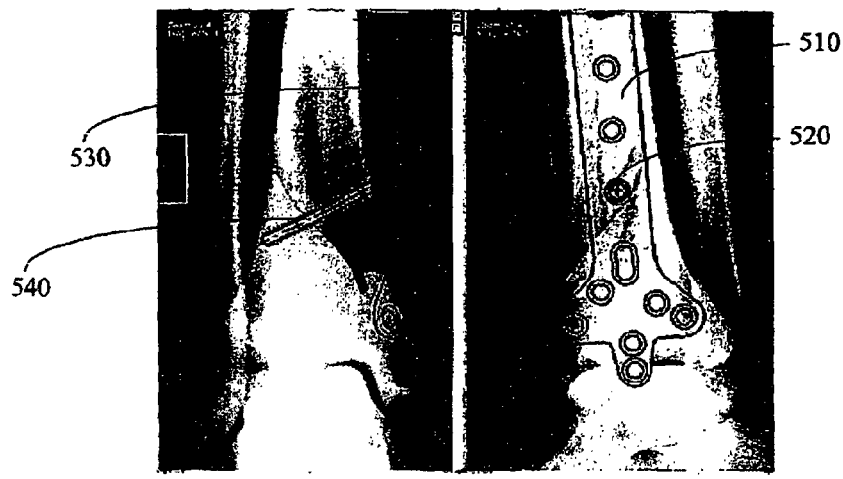
FIG. 5A is a schematic view of X-Ray image of a bone with fixation elements.
FIG. 5B is a schematic view of X-Ray image of a different view of a bone with fixation elements.

FIG. 5A and FIG. 5B demonstrate the process of Application and manipulation of fixation elements 40 of FIG. 1. The base images are the reduced fracture images of FIGS. 4A and 4B. The medical expert chooses a plate and screws as fixation elements. The plate and one screw are demonstrated as 510 and 520 in FIG. 5A and 530 and 540 in FIG. 5B correspondingly. The medical expert manually chooses the plate from a pre-defined set, or alternatively he may design a customized plate for a specific case. The plate is places in the preferred place along the broken bone. Then, a screw 520 and 540 of FIGS. 5A and 5B correspondingly is selected from a predefined set of screws and again manually placed in the proper place. Interactive functions like drag-and-drop and rotate may be used interactively to perform the selection and placing of the fixation elements. When a fixation element is moved and placed manually on one View by the medical expert, the pre planning system of the present invention may place automatically the fixation element on the other view using the registration data obtained in Image Acquisition Module 10 of FIG. 1.

Figures 6A, 6B:
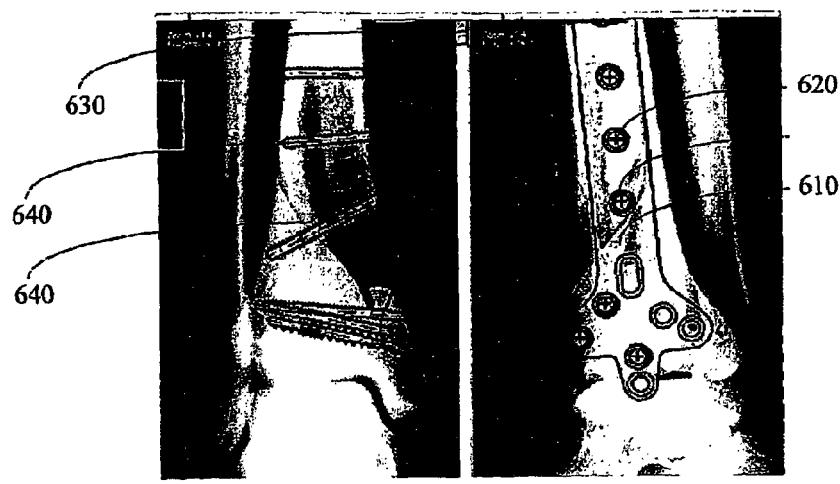
FIG. 6A is a schematic view of a full pre-operative plan in accordance with the present invention.
FIG. 6B is a schematic view of a different view of a full pre-operative plan in accordance with the present invention.

FIG. 6A and FIG. 6B demonstrate the two views of a final desired fixation application as pre planned by the pre planning system of the present invention. The fixation plate 610 and 630 of FIGS. 6A and 6B correspondingly is fixed to the bone segments by screws 620 and 640 of FIGS. 6A and 6B correspondingly. The medical staff is able to use the pre operative plan of FIGS. 6A and 6B during a surgical orthopedic procedure on the patient.

Figures 7A, 7B:
FIG. 7A is a schematic view of a post-operative result in accordance with the present invention.
FIG. 7B is a schematic view of a different view of a post operative result in accordance with the present invention.

FIGS. 7A and 7B demonstrate the actual postoperative result including actual plate 710 of FIG. 7A, and actual screws 730 of FIG. 7B. The postoperative result may be compared to the pre operative plan for evaluating the results of the surgical procedure and for educational purposes.

Figure 8A:
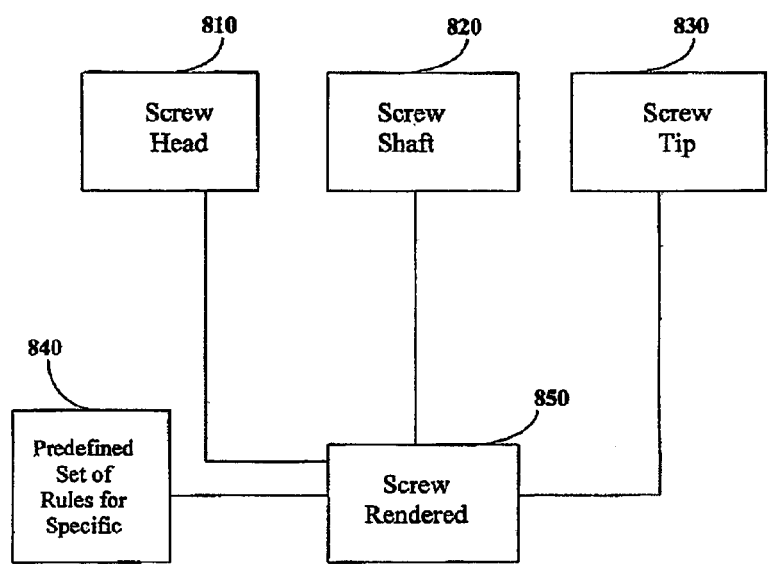
FIG. 8A is a flowchart describing rendering of a screw in accordance with the present invention.
Figure 8B:
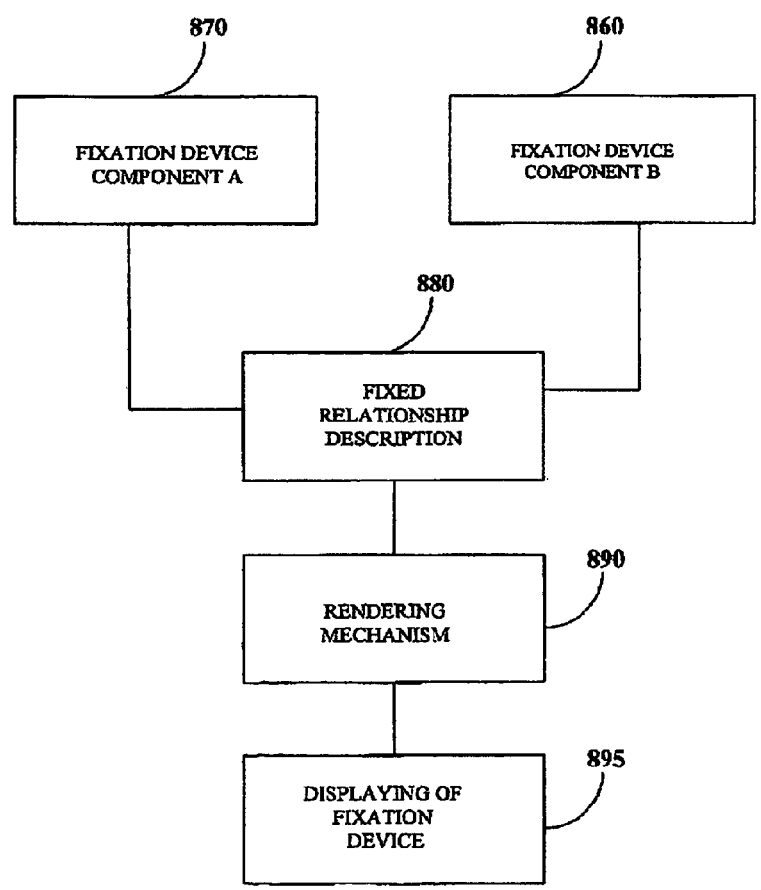
FIG. 8B is a flowchart describing rendering of a fixation device in accordance with the present invention.

Reference is now made to FIGS. 8A and 8B, that illustrate rendering of fixation elements.

In FIG. 8A, a Screw Head 810 is selected together with Screw Shaft 820, and a Screw Tip 830. Additional parameters and rules are selected from Predefined set of rules 840, and the system composes the Screw Rendered 850. Various screw as well as other elements can be defined using the same method, and it should be noted that fixation elements that are rendered this way are predefined to be available from a physical inventory.

FIG. 8B demonstrates composition of a fixation device composed of two fixation elements: Fixation Device Component A 870 and Fixation Device Component B 860. Fixed Relationship Description 880 defines the geometric relative positioning of Fixation Device Component A 870 and Fixation Device Component B 860. Rendering Mechanism 890 is used for storing and displaying the fixation device in step 895.

FIG. 9 is a flowchart of the process of osteotomy with external artificial fixation devices in accordance with the present invention. The process describes a generic mechanism for measurement deformity parameters that are difficult to measure using manual tools. The method provides a mechanism for AP translation and angulations, LT translation and angulations, axial translation, that is well suited for 3D models.

Selection anatomical/mechanical axis 900 is followed by planning a corrective procedure 905. Reference fragment selection 910 also includes marking of some organ segments. In step 915, the geometry and level of osteotomy are selected. Step 920 includes automatic calculation of parameters describing ambulation and translation. Calculation of impaction prevention 930 is necessary for enabling the whole process of osteotomy. This step includes planning of actual movements of organ segments and fixation elements selected in step 940. The process is concluded in step 950, which is performing simulation of the procedure by rotating the non-reference fragment (segment) around the calculated Cora.

Figure 10:
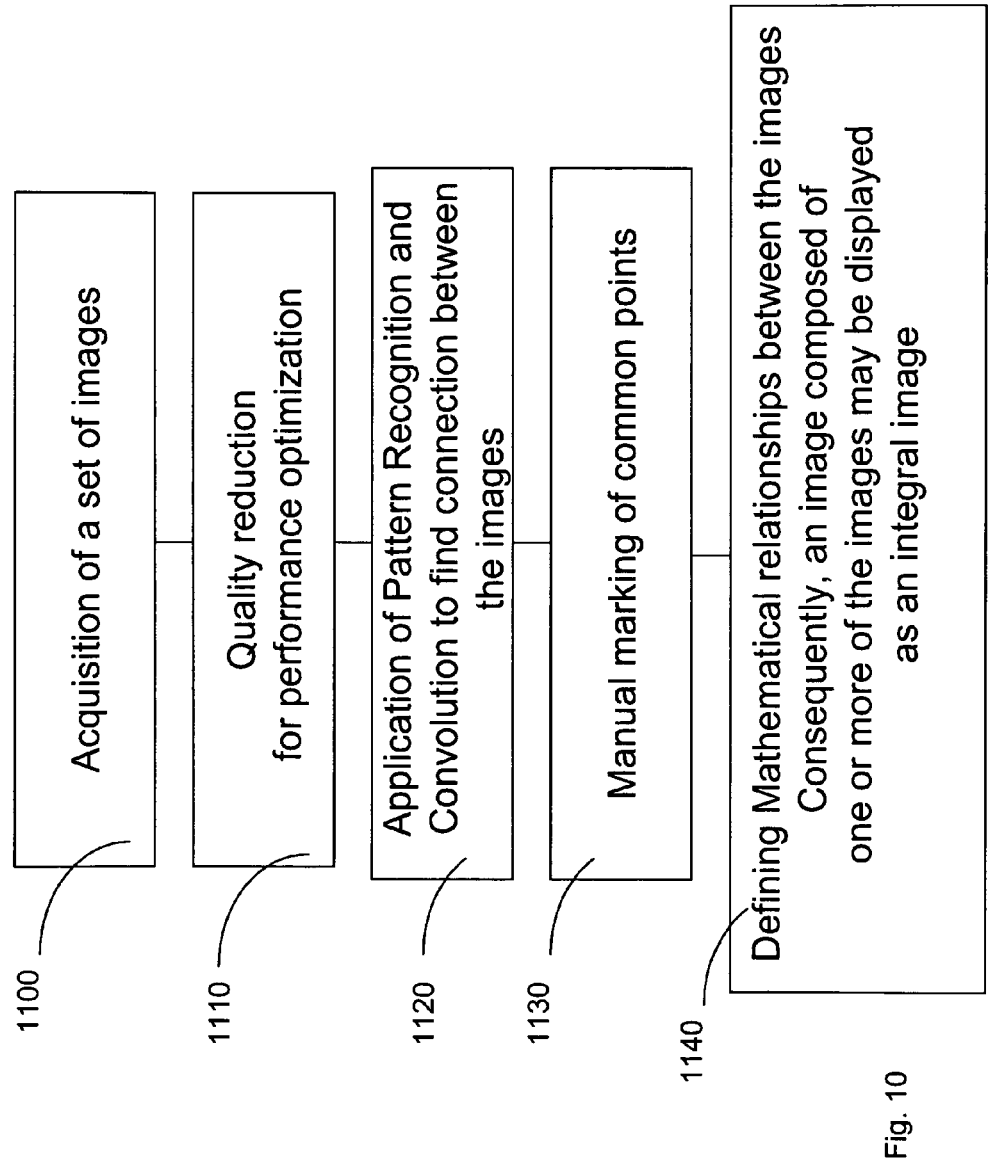

FIG. 10 is a detailed flowchart of automatic image rendering in accordance with the present invention. As explained hereinbefore, in Image rendering 15 of FIG. 1, separate images of different parts of an organ may be composed and integrated to a full image of the organ. The full image may be composed manually or automatically using image-processing algorithms. FIG. 10 illustrates automatic image rendering. It should be noted that many algorithms might be used for this purpose as part of the embodiment of the present invention. The algorithm described here is brought here just as one example. Acquisition of a set of images 1100 is followed by Quality reduction 1110. In step 1120 common points of several images are defined using pattern recognition and convolution techniques. Interactive manual assistance, namely Manual marking of common points 1130, which is performed by a medical expert may also be applied. As result, in step 1140 mathematical relationships between images is defined, and an image that is composed of various images may be displayed as an integral image.

Figure 11:
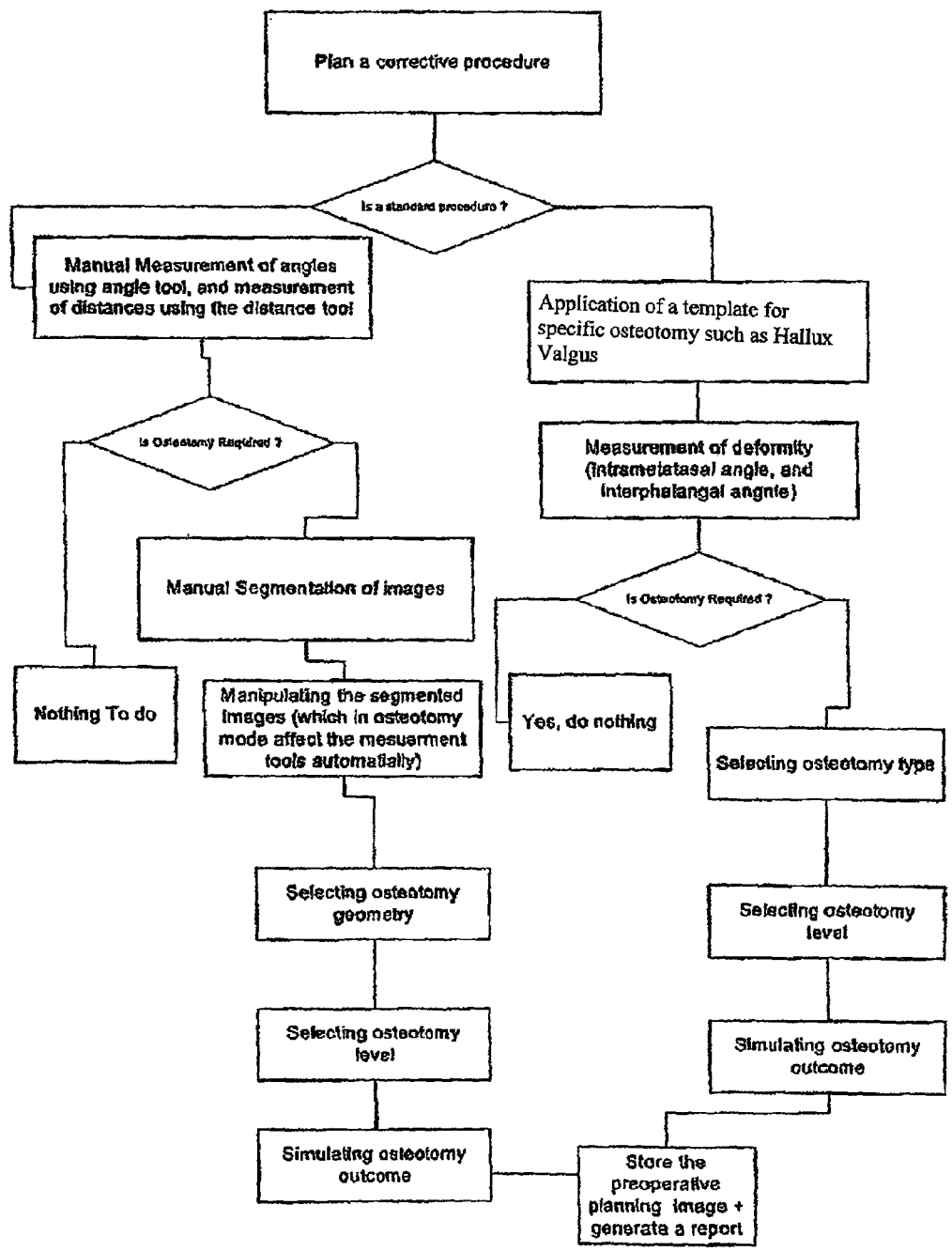
FIG. 11 is a flowchart of image rendering in accordance with another embodiment present invention.

Reference is made now to FIG. 11 that demonstrates the implementation of osteotomy simulation mechanism according to yet another embodiment of the present invention. It contains templates for frequent used surgical procedures such as high tibial osteototomy, or osteotomy of the first metatarsal of the foot (i.e., Hallux Valgus). It is acknowledged in this respect that other osteotomies, also those that are currently not fully implemented in the software, may also be preformed using the aforementioned manual osteotomy mechanism. The acquisition of images are displayed in diagram 11: at this first stage a medical professional is asked to select a procedure form a plurality of medical procedures supported by the software.

The software is presently an effective measurement tool for specific anatomy. The system can be automatic or must require an additional help of a medical professional place measurement tools on the specified anatomy. Once the positioning of the anatomy is achieved, the system automatically calculates deformity parameters, such as angulations and translation. According to this embodiment and in a non-limiting manner, using these parameters, a recommendation can be made regarding the treatment type, as well as its necessity. Osteotomy type is selected, including wedge geometry, and center of rotating and angulations and translation is automatically determined by the system or set manually by the medical professional. The System automatically performs the corrective procedure on the x-ray image, providing the surgeon with an output of how the treated anatomical structure is going to be affected by the procedure.

It is also in the scope of the present invention wherein a non standard procedure is provided. The Medical professional is directed to manually apply measurement tools, e.g., standard tools as ruler, angle tool, orthogonal line tool, as well as other tools, which assist in determining the nature of the pathology. Accordingly, the physician can select the rotating and moving parts of the anatomy taking into account osteotomy level and wedge geometry. Subsequently, he is advised to move or rotate one or more of the affected structures towards the desired position according to the geometry of the desired procedure.

We claim:

1. A method of image manipulation in an imaging apparatus for preoperative planning and simulating of an orthopedic surgical procedure to be performed on an anatomical structure, the planning being carried out on medical images that are direct images of the anatomical structure to be operated on, the method comprising inter alia:

a. providing a real dimension unit in said imaging apparatus, said real dimension unit defining an absolute length, thereby to provide said absolute length to appear in an image alongside said anatomical structure of a patient to be operated on to provide an image defining a calibration of the imaged anatomical structure alongside said anatomical structure of the patient to be operated on;

b. obtaining and displaying in said imaging apparatus the obtained direct medical images of the anatomical structure along with said calibration from said real dimension unit, prior to said orthopedic surgical procedure;

c. applying a non-linear imaging-device specific correction function to said direct medical images, to reduce device-specific distortion in said direct medical images, and thereby form corrected medical images;

d. creating a mathematical relationship between respective ones of said corrected medical images which are different projections of a view, thereby to allow three-dimensional assessment of said corrected medical images;

e. using said real dimension unit calibration and said mathematical relationship, determining from said corrected medical images an extent of trauma present in said anatomical structure;

f. segmenting the corrected medical images of the anatomical structure to be operated on into longitudinal structural segments in said imaging apparatus prior to said orthopedic surgical procedure, said longitudinal structural segments being in an original arrangement over said anatomical structure, the anatomical structure comprising bones and the segmentation comprising longitudinal structural segmentation of the image of the bone to be operated on, to form independently movable bone longitudinal structure part image segments to represent said trauma present in said bones; and g. using the segmented medical image in said imaging apparatus, said segmented image comprising said calibrated imaged anatomical structure of said patient to be operated on, planning, directly on said movable bone longitudinal structure part image segments of said bones to be operated on, a result of the orthopedic surgical procedure to be performed on the anatomical structure to reduce said trauma present in said bone, by rearranging of said movable bone longitudinal structure part image segments of said bones from said original arrangement to simulate said result within said anatomical structure and producing calibrated output images comprising said movable bone longitudinal structure part image segments rearranged to reduce said trauma, said rearranged movable bone longitudinal structure part image segments providing said preoperative planning.

2. The method according to claim 1, further comprising dynamic rendering of medical device from pre defined members, the method allowing dynamic rendering of medical devices with a pre defined relationship, wherein two or more members can be integrated to one member in runtime according to a predefined rule.

3. The method according to claim 1, wherein said direct medical images are X-ray images.

4. The method according to claim 1, wherein said direct medical images comprise a combination of imaging techniques.

5. The method according to claim 1, wherein said direct medical images comprise a plurality of views of said anatomical structure.

6. The method according to claim 1, wherein the obtaining step comprises transforming of said medical images to digital images.

7. The method according to claim 1, wherein said obtaining includes composing of several images of the same anatomical structure into a full-length view of said anatomical structure.

8. The method according to claim 1, wherein the obtaining step comprises calibrating of images.

9. The method according to claim 8, wherein said calibrating comprises registration of different views.

10. The method according to claim 8, wherein said calibrating comprises dimension and orientation calibration.

11. The method according to claim 8, wherein said calibrating comprises using image enhancements, said image enhancements comprising at least one member of the group consisting of brightness adjustments, contrast adjustments, and edge detection.

12. The method according to claim 1, wherein the segmenting step comprises one member of the group of ways consisting of: manual performance by a medical expert, automatic performance, wherein the anatomical structure segments are segmented according to predefined rules, and semi-automatic performance, wherein the segmenting step is performed automatically with the assistance of a medical expert.

13. The method according to claim 1, wherein said rearranging comprises simulating different positioning of said movable bone longitudinal structure part image segments.

14. The method according to claim 13, wherein said different positioning of said movable bone longitudinal structure part image segments relates to reducing of said trauma during trauma treatment.

15. The method according to claim 13, wherein said different positioning of said movable bone longitudinal structure part image segments relates to pre designed osteotomy treatments.

16. The method according to claim 1, further comprising inserting implants, in the manner that superposition of implants and said segmented anatomical structure over non-segmented fragments of said anatomical structure is provided.

17. The method according to claim 1, further comprising choosing a plurality of fixation elements from a predefined database.

18. The method according to claim 17, further comprising rules for correct positioning of said fixation elements so incorrect positioning of said fixation elements is prevented.

19. The method according to claim 1, wherein said planning comprises producing and storing the output images and planning reports of a plurality of alternatives of said steps of segmenting and planning, so that the best alternative for medical treatment is selected from said alternatives; said planning report comprising a part definition of calibrated artificial elements selected for the treatment as well as patient information.

20. The method according to claim 19, additionally comprising providing hard copies of said output images and said planning reports of a selected set of said alternatives.

21. The method according to claim 19, additionally comprising communicating said output images and said planning reports to a plurality of remote users.

22. The method according to claim 1, wherein said real dimension unit comprises an object of a known length.

23. The method according to claim 1, wherein said medical images of the anatomical structure are imaged on an imager remote from the location of the orthopedic surgical procedure.

24. The method of claim 1, wherein said obtained output images further comprise, at least one feature selected from the group consisting of: a plurality of calibrated organs; a plurality of calibrated artificial elements; and at least one superposition of said calibrated artificial elements on said calibrated organs or organ segments.

25. An apparatus for pre-planning and simulating of an orthopedic surgical procedure to be performed on an anatomical structure of a patient suffering a trauma, said preplanning carried out directly on medical images taken of the anatomical structure to be the subject of the surgical procedure, the apparatus comprising;

a. a real dimension unit defining an absolute length, to provide said absolute length to appear in a direct medical image of said anatomical structure, said real dimension unit appearing alongside said anatomical structure to be the subject of the surgical procedure to provide a calibrated direct medical image of said anatomical structure;

b. a non-linear corrector for applying a non-linear imaging-device specific correction function to said direct medical images, to reduce device-specific distortion in said direct medical images, thereby to provide a corrected direct medical image;

c. a projection linker for creating a mathematical relationship between respective ones of said corrected direct medical images which are different projections of a view, thereby to allow three-dimensional assessment of said images;

d. a segmenting unit for defining and marking longitudinal anatomical structure segments in an original arrangement in the corrected direct medical image of the anatomical structure to be the subject of the surgical procedure, the anatomical structure comprising bones of said patient and the image structure segments being direct image structural segments of said bones of said patient, said direct image structural segments being independently movable;

e. a planning unit for planning a result of said orthopedic surgical procedure to be performed on the anatomical structure to minimize said trauma, the direct image having said real dimension unit calibration to estimate an extent of said trauma, the planning unit comprising a rearranger for rearranging of said direct image anatomical structure longitudinal segments from said original arrangement to simulate said result within said anatomical structure thereby to produce calibrated output images, the calibrated output images comprising said direct image anatomical structure bone segments of said patient being rearranged;

f. a memory for storing said medical images and a desired result; and, g. a display for displaying said calibrated medical images and said output images.

26. The apparatus according to claim 25, further comprising means for dynamic rendering of medical device from pre defined members, allowing dynamic rendering of medical devices with a pre defined relationship, wherein two or more members can be integrated to one member in runtime according to a predefined rule.

27. The apparatus according to claim 25, wherein the direct medical images are X-ray images.

28. The apparatus according to claim 25 wherein the direct medical images are combination of a plurality of imaging techniques.

29. The apparatus according to claim 25, wherein the direct medical images comprise a plurality of views of the same anatomical structures.

30. The apparatus according to claim 25, additionally comprising a transforming device for transforming said medical images to digital images.

31. The apparatus according to claim 25, additionally composing a composing device for composing of several images of the same anatomical structure into a full-length view of said anatomical structure.

32. The apparatus according to claim 25, additionally comprising a calibration device for images.

33. The apparatus according to claim 32, wherein the calibration device is also utilized for registration of different views.

34. The apparatus according to claim 32, wherein the calibration device is also utilized for dimension and orientation calibration.

35. The apparatus according to claim 32, wherein the calibration device is also utilized for image enhancements.

36. The apparatus according to claim 32, wherein the calibration device is also utilized for correction of image distortions.

37. The apparatus according to claim 25, further comprising a segmenting device, wherein the segmenting device is manually operated by a medical expert, or wherein the segmenting device is automatically operated according to predefined rules, or wherein the segmenting device is operated semi-automatically in the manner that the segmenting step is performed automatically with the assistance of a medical expert.

38. The apparatus according to claim 25, further comprising a planning device, wherein the planning device is additionally utilized for simulating different positioning of said anatomical structure segments.

39. The apparatus according to claim 38, wherein said different positioning of said anatomical structure segments relates to pre designed osteotomy treatments for deformed anatomical structures.

40. The apparatus according to claim 25, further comprising a planning device, wherein the planning device is utilized for simulating reduction of fractures during trauma treatment.

41. The apparatus according to claim 25, further comprising implants, for superposition in the manner that superposition of implants and said segmented anatomical structure over non-segmented fragments of said anatomical structure is provided.

42. The apparatus according to claim 25, further comprising a predefined database comprising predefined sets of fixation elements.

43. The apparatus according to claim 42, further comprising a positioning device for correct positioning of said fixation elements so incorrect positioning of said fixation elements is prevented.

44. The apparatus according to claim 25, additionally comprising a report preparation and storage device for producing and storing planning reports of a plurality of alternative treatments, thereby to ensure that the best alternative for medical treatment is selected from said alternatives, said planning reports comprising a part definition of a treatment using calibrated artificial elements selected according to the medical treatment and patient information.

45. The apparatus according to claim 44, additionally comprising a hard copy producer configured to produce hard copies of said output images and said planning reports of a selected set of said alternatives.

46. The apparatus according to claim 44, additionally comprising a communication device for communicating said output images and said planning reports to remote users.

47. The apparatus according to claim 25, wherein said displayed image comprises a final image for the orthopedic surgical procedure.

* * * * *